United States Patent
Ben Ezer et al.

(10) Patent No.: US 10,215,707 B2
(45) Date of Patent: Feb. 26, 2019

(54) SYSTEM FOR INSPECTING A BACKSIDE OF A WAFER

(71) Applicant: CAMTEK LTD., Migdal-Haemek (IL)

(72) Inventors: Zehava Ben Ezer, Moshav Balfuria (IL); Guy Kafry, Atzmon Segev (IL); Shimon Koren, Haifa (IL); Eldad Langmans, Haifa (IL); Natan Deutsch, Kfar Pines (IL)

(73) Assignee: CAMTEK LTD., Higdal Haemek (IL)

( * ) Notice: Subject to any disclaimer, the term of this patent is extended or adjusted under 35 U.S.C. 154(b) by 185 days.

(21) Appl. No.: 15/207,537

(22) Filed: Jul. 12, 2016

(65) Prior Publication Data

US 2017/0010220 A1  Jan. 12, 2017

Related U.S. Application Data

(60) Provisional application No. 62/191,430, filed on Jul. 12, 2015.

(51) Int. Cl.
*G01N 21/88* (2006.01)
*H04N 7/18* (2006.01)
*H04N 5/225* (2006.01)
*G01N 21/95* (2006.01)

(52) U.S. Cl.
CPC ..... *G01N 21/8806* (2013.01); *G01N 21/9501* (2013.01); *H04N 5/2256* (2013.01); *H04N 5/2257* (2013.01); *H04N 7/183* (2013.01); *G01N 2021/8825* (2013.01)

(58) Field of Classification Search
CPC ......... H01L 2924/0002; H01L 2924/00; H01L 25/0753; H01L 2924/1815; H01L 33/54; G01N 2021/8825; G01N 21/8806; G01N 21/9501
See application file for complete search history.

(56) References Cited

U.S. PATENT DOCUMENTS

| | | | | |
|---|---|---|---|---|
| 5,917,588 A | * | 6/1999 | Addiego | G01N 21/8806 356/237.2 |
| 2013/0016206 A1 | * | 1/2013 | Zimmer | G01N 21/9501 348/87 |

\* cited by examiner

*Primary Examiner* — Michael P Stafira
(74) *Attorney, Agent, or Firm* — Reches Patents

(57) ABSTRACT

An inspection system for inspection a surface of a substrate, the inspection system may include an interface for holding the substrate; a movement mechanism for moving the interface, thereby moving the substrate between different positions; a bright field light source that is configured to illuminate different bright field illuminated parts of the surface of the substrate when the substrate is positioned at the different positions; at least one dark field light source that is configured to illuminate different dark field illuminated parts of the surface of the substrate when the substrate is positioned at the different positions; and a camera that is configured to: (a) generate bright field detection signals in response to light that is detected by the camera as a result of the illumination of the different bright field illuminated parts; and (b) generate dark field detection signals in response to light that is detected by the camera as a result of the illumination of the different dark field illuminated parts; and wherein light that is detected by the camera as the result of the illumination of the different bright field illuminated parts and as the result of the illumination of the different dark field illuminated parts does not include an image of the camera.

35 Claims, 16 Drawing Sheets

SYSTEM FOR INSPECTING A BACKSIDE OF A WAFER

CROSS REFERENCE TO RELATED APPLICATIONS

This application claims the priority of U.S. provisional patent Ser. No. 62/191,430 filing date Jul. 12, 2015 which is incorporated herein in its entirety.

BACKGROUND OF THE INVENTION

Semiconductor wafers have a backside that should be inspected for detecting defects and monitoring the quality of the wafer.

There is a growing need to provide a system for inspecting a backside of a wafer.

SUMMARY

According to an embodiment of the invention there may be provided an inspection system for inspection a surface of a substrate, the inspection system may include an interface for holding the substrate; a moving mechanism for moving the interface, thereby moving the substrate between different positions; a bright field light source that may be configured to illuminate different bright field illuminated parts of the surface of the substrate when the substrate is positioned at the different positions; at least one dark field light source that may be configured to illuminate different dark field illuminated parts of the surface of the substrate when the substrate is positioned at the different positions; and a camera that may be configured to: (a) generate bright field detection signals in response to light that is detected by the camera as a result of the illumination of the different bright field illuminated parts; and (b) generate dark field detection signals in response to light that is detected by the camera as a result of the illumination of the different dark field illuminated parts; and wherein light that is detected by the camera as the result of the illumination of the different bright field illuminated parts and as the result of the illumination of the different dark field illuminated parts does not include an image of the camera.

The moving mechanism may be a rotating mechanism for rotating the interface thereby rotating the substrate between different positions.

The surface of the substrate may be a backside of the substrate.

The at least one dark field light source and the bright field light source may be configured to illuminate the backside of the substrate in a non-overlapping manner.

The substrate may be positioned at the different positions during different time periods; and wherein during at least one time period the bright field light source and the at least one dark field light source may be configured to concurrently illuminate the backside of the substrate.

For each bright field illuminated part of the different bright field illuminated parts, when the bright field illuminated part is illuminated, an optical axis of the camera virtually crosses a substrate backside plane the at a first crossing point that may be located outside the bright field illuminated part; and wherein the backside of the substrate is located within the substrate backside plane.

For each dark field illuminated part of the different dark field illuminated parts, when the dark field illuminated part is illuminated, an optical axis of the camera virtually crosses a substrate backside plane the at a crossing point that may be located outside the dark field illuminated part; and wherein the backside of the substrate is located within the substrate backside plane.

The interface may include different interface portions for supporting substrates of different sizes.

The different interface portions may be coaxial and may be positioned at different heights.

The inspection system may include an alignment sensor and a controller; wherein the interface may include an alignment target; wherein alignment sensor may be configured to detect the alignment target; and wherein the controller may be configured to control the movement mechanism in response to detection signals from the alignment sensors.

The controller may be configured to maintain an alignment between an orientation of the substrate when the substrate is received by the inspection system and between an orientation of the substrate at an end of an inspection of the substrate.

The bright field light source may be a flat dome that faces the backside of the substrate.

The at least one dark field light source may include multiple dark field light sources.

The multiple dark field light sources may be configured to illuminate the backside of the substrate from different directions.

The multiple dark field light sources may be four dark field light sources that may be perpendicular to each other.

The multiple dark field light sources, the bright field light source and the camera may be mechanically coupled to a supporting structure.

The supporting structure may be a frame; wherein the bright field light source may be positioned within the frame; and wherein the camera and the multiple dark field light sources may be positioned outside the frame.

The substrate, when held by the interface, may be positioned directly above a portion of the bright field light source.

The multiple dark field light sources may be arranged in an asymmetrical manner in relation to an axis of rotation of the interface.

An axis of rotation of the interface may virtually cross the bright field light source at a second crossing point that may be spaced apart from a center of the bright field light source.

The bright field light source has a first side and a second side that may be opposite to each other; wherein the camera may be closer to the first side of the bright field light source; and wherein a distance (denoted 411 in FIG. 13) between the second crossing point and the camera may be a fraction of a distance (denoted 412 in FIG. 13) between the second crossing point and the second side of the bright field light source.

The camera and the bright field light source may be positioned at substantially a same distance from a substrate backside plane in which the backside of the substrate is located.

A distance (denoted 421 in FIG. 12) between the dark field light source and a substrate backside plane may be smaller than a distance (denoted 422 in FIG. 12) between the camera and the substrate backside plane and may be smaller than a distance (denoted 423 in FIG. 12) between the bright field light source and the substrate backside plane, wherein the backside of the substrate is located at the substrate backside plane.

The movement mechanism may be configured to rotate the substrate by a rotation that substantially equals half a cycle between one position of the different positions to another position of the different positions.

The movement mechanism may be configured to rotate the substrate by a rotation that substantially equals a fraction of a cycle between one position of the different positions to another position of the different positions, wherein the fraction of the cycle may be smaller than half a cycle.

An optical axis of the camera may be normal to the backside of the substrate.

A shape of the backside of the substrate substantially equals a circle; wherein at least some of the dark field illuminated parts and the bright field illuminated parts have a shape that delimited by a single chord and an arc that may be connected to the single chord; and wherein the single chord may be smaller than a diameter of the backside of the substrate. FIGS. 4A-4C illustrates first chord 401 and second chord. FIG. 4E illustrates first chord 401, second chord 402 and third chord 403.

The inspection system may include a processor that may be configured to process the bright field detection signals and the dark field detection signals.

The inspection system may include a processor that may be configured to reconstruct one or more images of the substrate; wherein the one or more images may include a bright field image of the backside of the substrate and a dark field image of the backside of the substrate.

The inspection system may include a processor; wherein the processor may be configured to reconstruct a bright field image of the backside of the substrate from bright field detection signals related to the different bright field illuminated parts of the backside of the substrate.

The interface may include alignment targets; wherein the processor may be configured to reconstruct the bright field image of the backside of the backside of the substrate based on bright field detection signals related to the alignment targets.

The inspection system may include a processor; wherein the processor may be configured to reconstruct bright field images of the different bright field illuminated parts of the backside of the substrate from the bright field detection signal related to the different bright field illuminated parts of the backside of the substrate; wherein the bright field images of the different bright field illuminated parts of the backside of the substrate comprise images the alignment target.

The processor may be configured to merge the bright field images of the different bright field illuminated parts of the backside of the substrate to provide the bright field image of the backside of the backside; wherein the merging may be responsive to the images of the alignment targets.

The interface may include different interface portions for supporting substrates of different sizes; wherein each of the different interface portions may include a subset of the alignment targets.

According to an embodiment of the invention there may be provided a method for inspecting a surface of a substrate, the method may include holding the substrate by an interface; moving the interface, thereby moving the substrate between different positions, by a movement mechanism; illuminating, by a bright field light source, different bright field illuminated parts of the surface of the substrate when the substrate is positioned at the different positions; illuminating, by at least one dark field light source, different dark field illuminated parts of the surface of the substrate when the substrate is positioned at the different positions; and generating, by a camera, (a) bright field detection signals in response to light that is detected by the camera as a result of the illumination of the different bright field illuminated parts; and (b) dark field detection signals in response to light that is detected by the camera as a result of the illumination of the different dark field illuminated parts; and wherein light that is detected by the camera as the result of the illumination of illumination of the different bright field illuminated parts and as the result of the illumination of the different dark field illuminated parts does not include an image of the camera.

According to an embodiment of the invention there may be provided a non-transitory computer readable medium that stores instructions that once executed by a computerized system such as but not limited to an inspection system, causes the computerized system to execute the steps of holding the substrate by an interface; moving the interface, thereby moving the substrate between different positions, by a movement mechanism; illuminating, by a bright field light source, different bright field illuminated parts of the surface of the substrate when the substrate is positioned at the different positions; illuminating, by at least one dark field light source, different dark field illuminated parts of the surface of the substrate when the substrate is positioned at the different positions; and generating, by a camera, (a) bright field detection signals in response to light that is detected by the camera as a result of the illumination of the different bright field illuminated parts; and (b) dark field detection signals in response to light that is detected by the camera as a result of the illumination of the different dark field illuminated parts; and wherein light that is detected by the camera as the result of the illumination of illumination of the different bright field illuminated parts and as the result of the illumination of the different dark field illuminated parts does not include an image of the camera.

BRIEF DESCRIPTION OF THE INVENTION

The present invention will be understood and appreciated more fully from the following detailed description taken in conjunction with the drawings in which.

DETAILED DESCRIPTION OF THE INVENTION

Because the apparatus implementing the present invention is, for the most part, composed of electronic components and circuits known to those skilled in the art, circuit details will not be explained in any greater extent than that considered necessary as illustrated above, for the understanding and appreciation of the underlying concepts of the present invention and in order not to obfuscate or distract from the teachings of the present invention.

In the following specification, the invention will be described with reference to specific examples of embodiments of the invention. It will, however, be evident that various modifications and changes may be made therein without departing from the broader spirit and scope of the invention as set forth in the appended claims.

The following examples refer to a wafer. The wafer is just a non-limiting of a substrate that can be inspected by the systems and method disclosed below.

The following refers to a rotation of a substrate and to a rotation mechanism. Rotation is merely a non-limiting example of moving the substrate and the rotation mechanism is a non-limiting example of a movement mechanism.

It is noted that the application describes the acquisition of images of various parts (for example a first part, a second part and the like) of a wafer. Each one of these parts may include a substantial (majority, about a half, not less than one fourth) part of the wafer- and in a sense the inspection disclosed in the application can be regarded as macro-inspection.

Any reference to a bright field illumination, field of view, camera may be applied mutatis mutandis to dark field illumination, field of view and camera—and vice versa.

The various figures illustrate inspection system 100, portions of the inspection system 100, a wafer, according to various embodiments of the invention.

Figure 1:
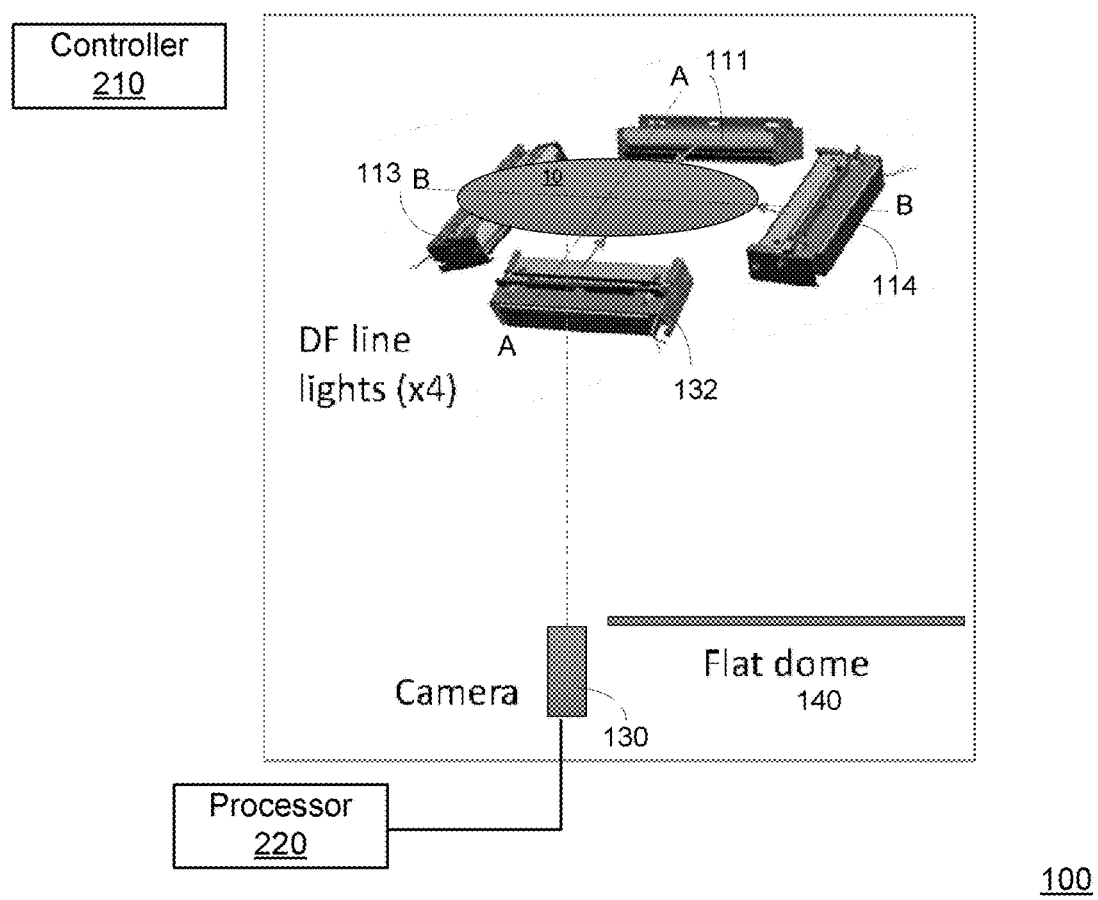
FIG. 1 illustrates a wafer and a portion of an inspection system according to an embodiment of the invention.
Figure 2A:
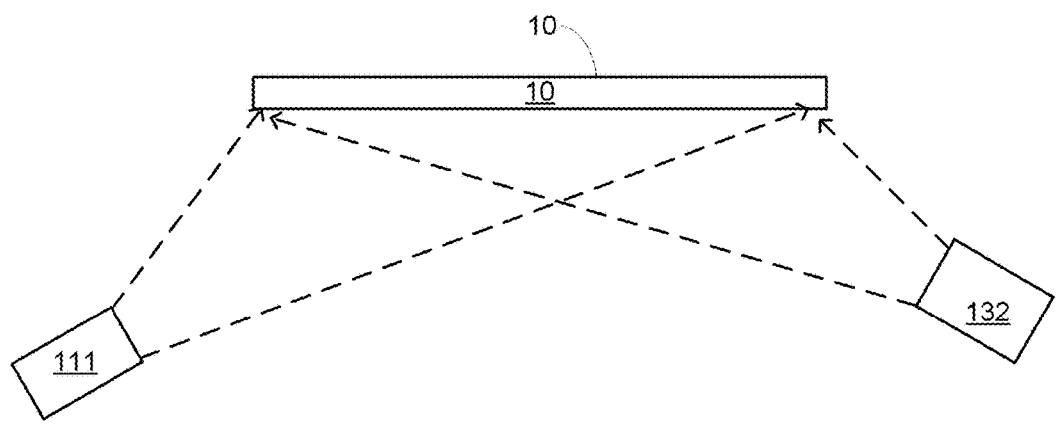
FIG. 2A illustrates fields of view of two dark field light sources according to an embodiment of the invention.
Figure 2B:
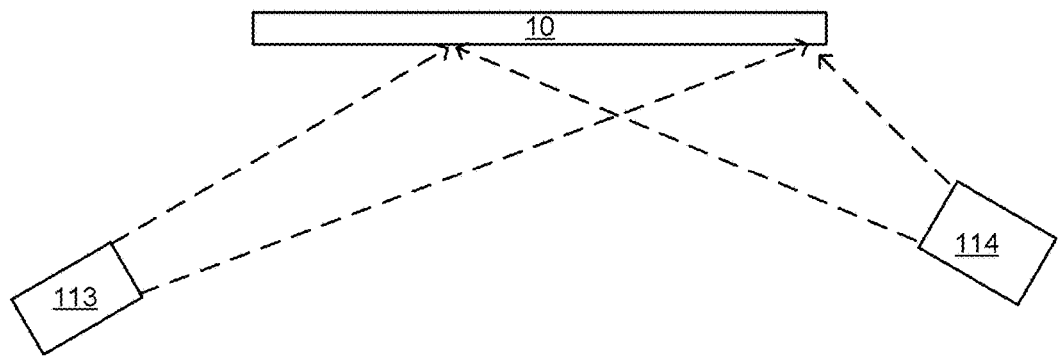
FIG. 2B illustrates fields of view of two other dark field light sources according to an embodiment of the invention.
Figure 3:
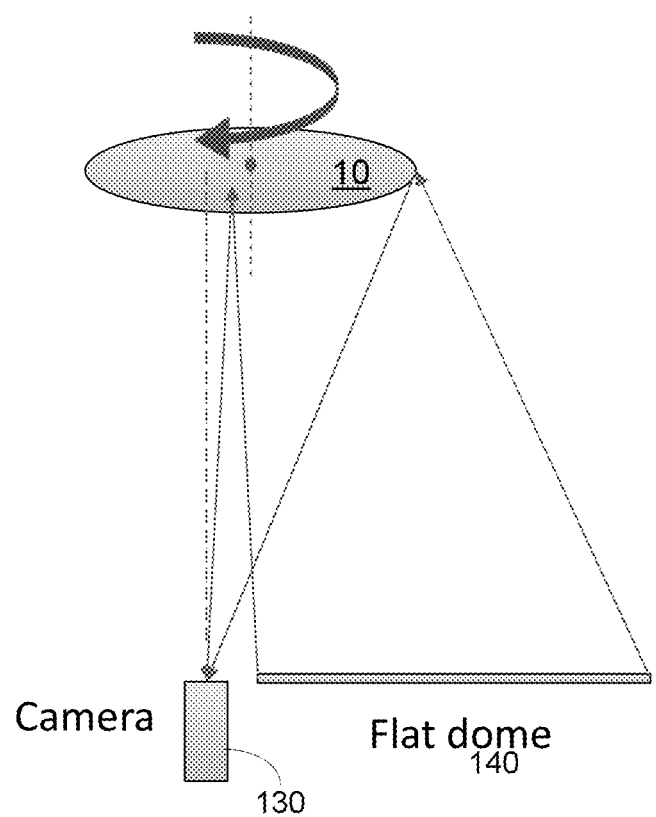
FIG. 3 illustrates a field of view of a bright field light sources according to an embodiment of the invention.
Figure 4A:
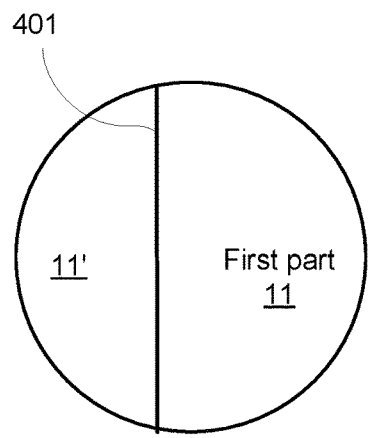
FIG. 4A illustrates a first bright field illuminated part of a backside of a wafer when the wafer is positioned at a first position according to an embodiment of the invention.
Figure 4B:
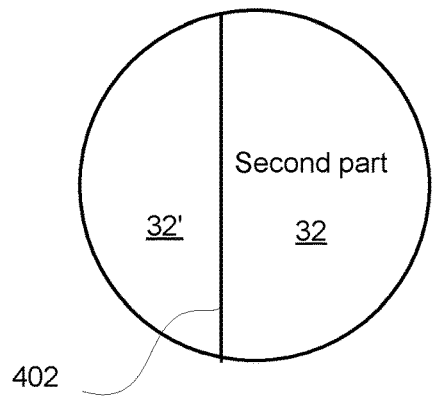
FIG. 4B illustrates a second bright field illuminated part of a backside of a wafer when the wafer is positioned at a second position according to an embodiment of the invention.
Figure 4C:
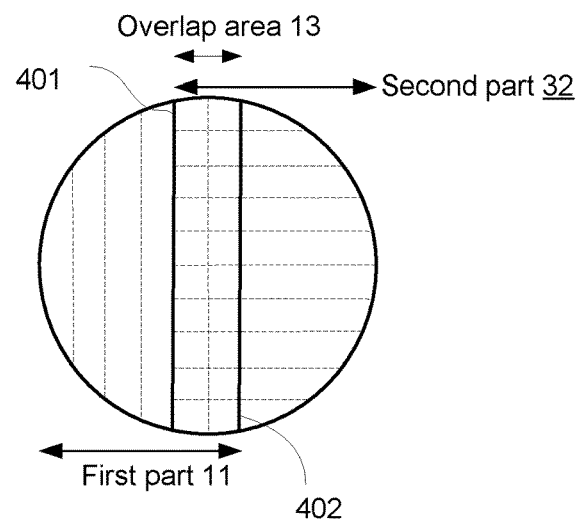
FIG. 4C illustrates the first and second bright field illuminated parts of the backside of a wafer that are overlaid and provide an overlap according to an embodiment of the invention.
Figure 4D:
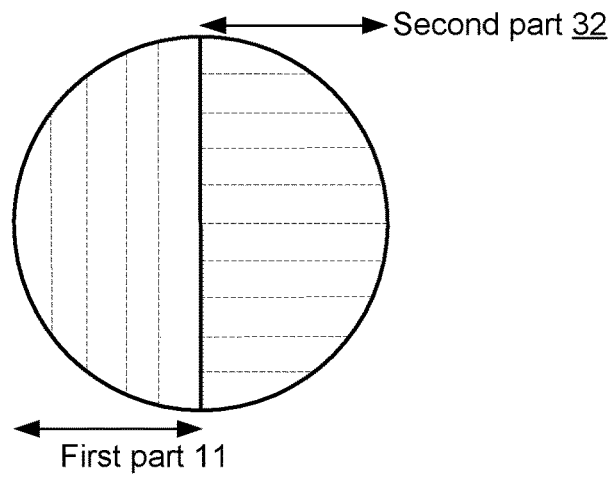
FIG. 4D illustrates the first and second bright field illuminated parts of the backside of a wafer that are overlaid without overlap according to an embodiment of the invention.
Figure 4E:
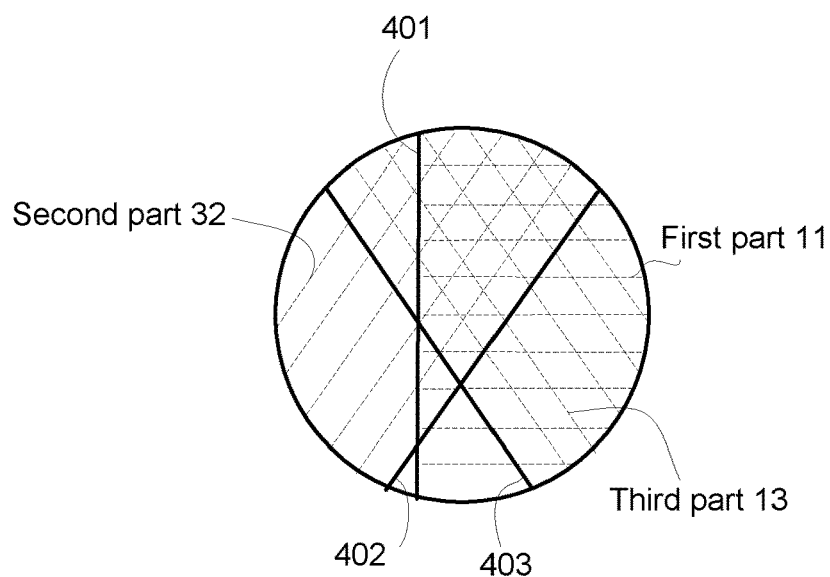
FIG. 4E illustrates the first and second bright field illuminated parts of the backside of a wafer and a third bright field illuminated part of the wafer that is illuminated when the wafer is at a third position according to an embodiment of the invention.

Inspection system 100 of FIG. 1 may be configured to:

a. Acquire one or more bright field images of a first part of the backside of the wafer. The first part may equal one half of the backside of the wafer or may exceed one half of the backside of the wafer.

b. Acquire one or more dark field images of the first part of the backside of the wafer. (See—FIG. 4—first part 11 that is illuminated and first residual part 11' that is not illuminated).

c. Rotate the wafer such as to expose a second part of the backside of the wafer to dark field and bright field image acquisition. The second part differs from the first side and may partially overlap the first side or not overlap at all.

d. Acquire one or more bright field images of the second part of the backside of the wafer. (See—FIG. 4—second part 12 that is illuminated and second residual part 12' that is not illuminated).

e. Acquire one or more dark field images of the second part of the backside of the wafer.

f. Store and/or send and/or process at least one image acquired during steps a-d. The processing may be done in order to detect defects and/or evaluate the quality of the backside and visible part of the edge of the wafer.

The first and second parts of the backside of the wafer may partially overlap to prevent a lack of coverage of wafer areas near the edges of the first and second parts of the backside of the wafer.

Although the system is illustrated as inspecting the wafer by two inspection iterations (first inspection iteration includes steps a and b, second inspection iteration includes steps e and d)—and a rotation of substantially 180 degrees between the inspection iterations. It is noted that the inspection system may execute more than two inspection iterations and that the rotation between one inspection iteration to another may differ from 180 degrees. It is further noted that the illumination sources and/or camera may be rotated while the wafer is maintained static or is moved. The rotation may be replaced by a non-rotational movement that allows to "cover" the backside of the wafer.

When bright field images are acquired—the wafer backside is illuminated by a bright field light source 140 such as the flat dome of FIGS. 1, 3, 6, 7, 11 and 12. The reflected light from the backside of the wafer is captured by camera 130. The detection signals of the camera (forming dark field images and/or bright field images) may be stored, sent to another system or processed by processor 220. System 100 may be controlled by controller 210.

When dark field images are acquired—the wafer backside is illuminated by dark field light sources such as dark field light sources 111, 112, 113 and 114 of FIGS. 1, 2, 6, 7, 11 and 12. The scattered light from the backside of the wafer is captured by camera 130. The dark field light sources illuminate the wafer from different direction and thus increase the quality of detection—assist in detecting defects that can be viewed from different orientations. The optical axis of the dark field sources may be adjustable (for example—by rotating the dark field light sources).

It is noted that the system may use different radiations or different polarizations and/or different cameras for acquiring bright field images and dark field images simultaneously.

Figure 5:
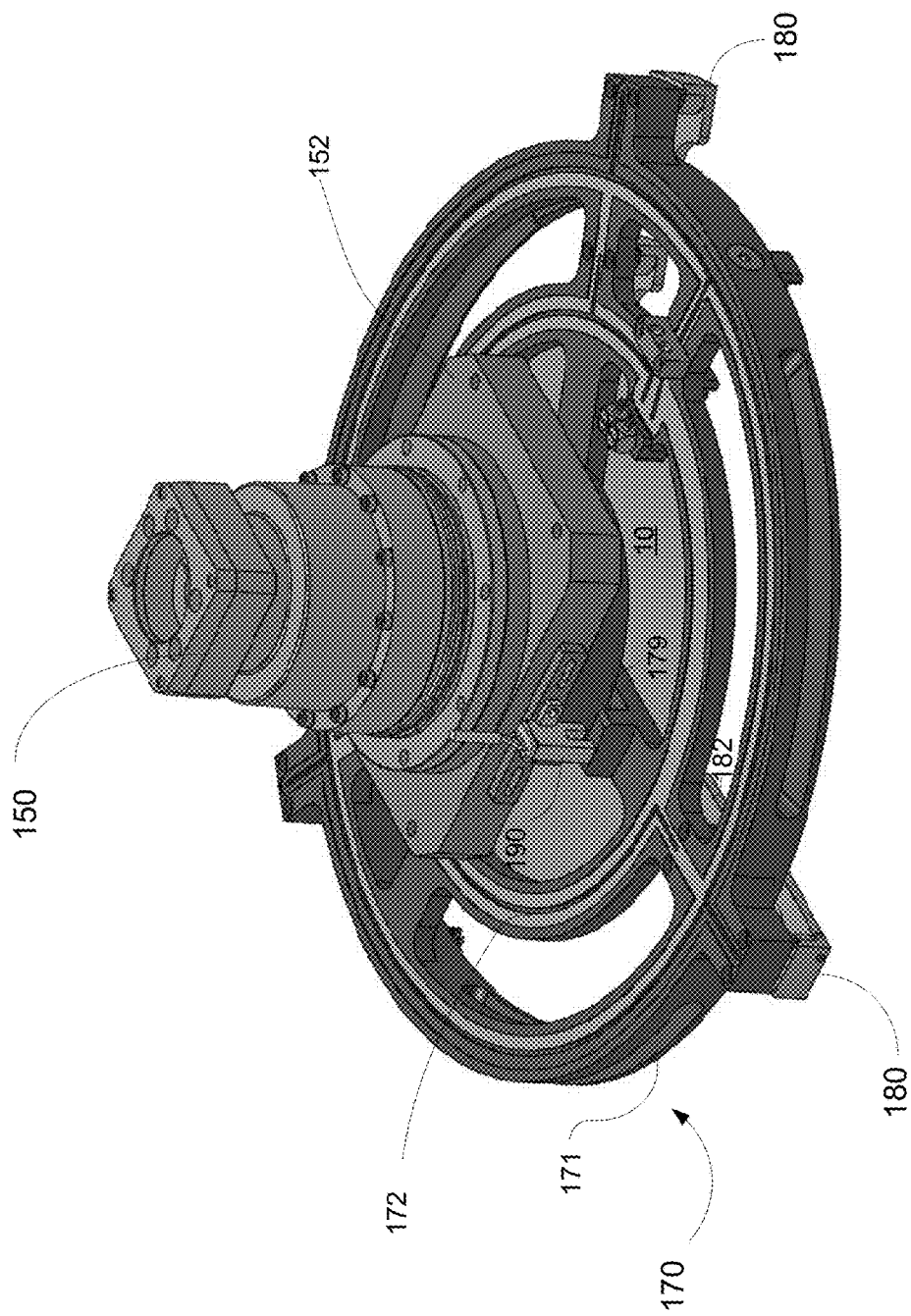
FIG. 5 illustrates a wafer and a portion of an inspection system according to an embodiment of the invention.
Figure 6:
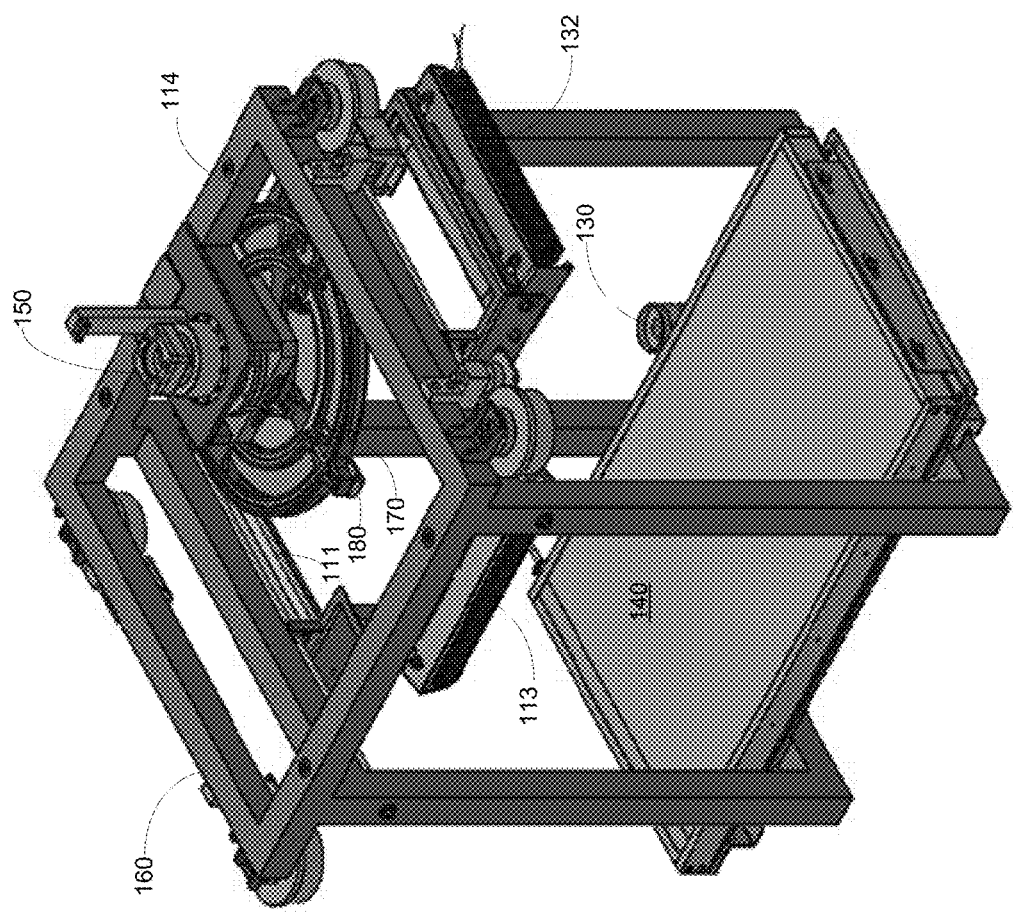
FIG. 6 illustrates a wafer and a portion of an inspection system according to an embodiment of the invention.
Figure 7:
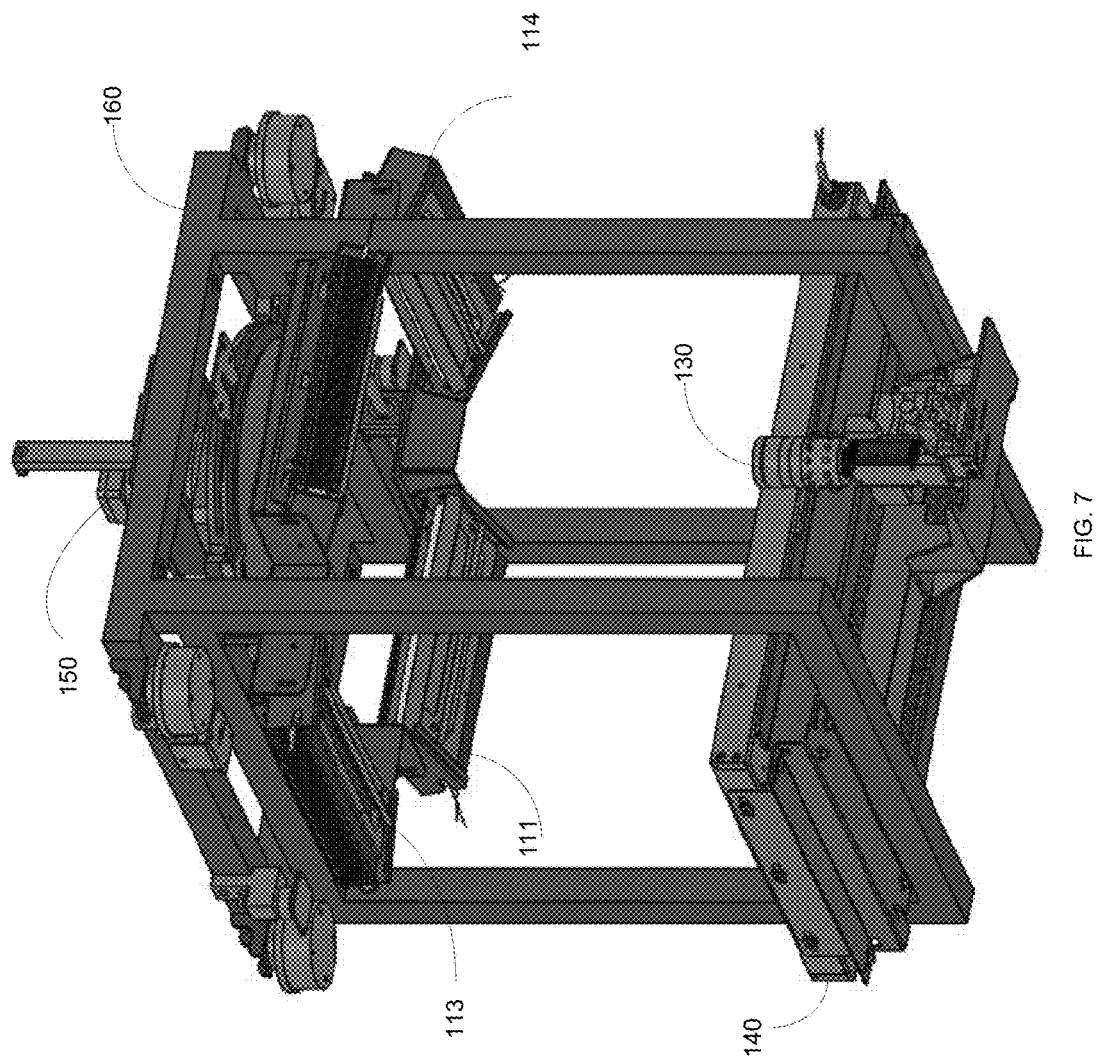
FIG. 7 illustrates a wafer and a portion of an inspection system according to an embodiment of the invention.
Figure 8:
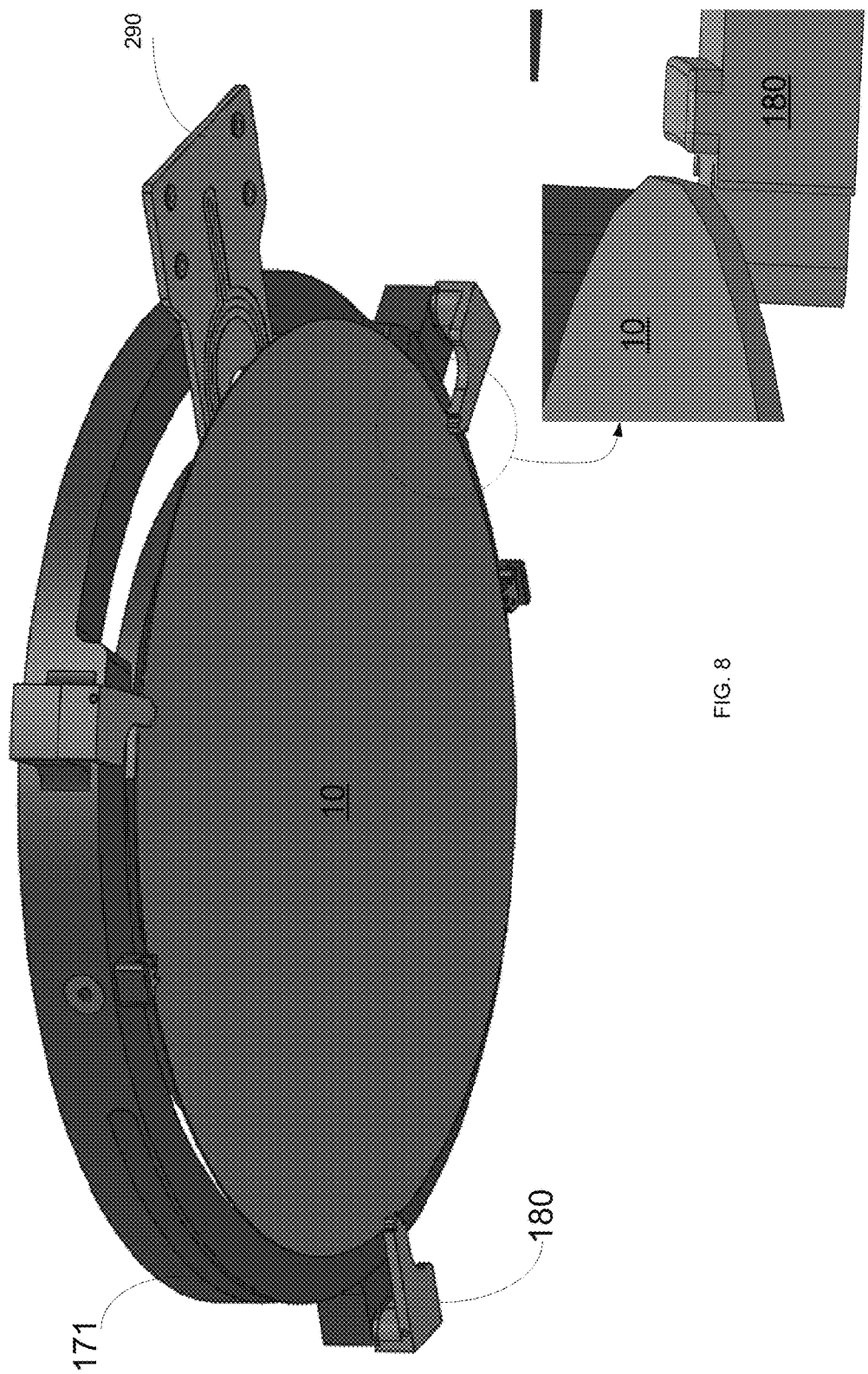
FIG. 8 illustrates a wafer and a portion of an inspection system according to an embodiment of the invention.

Wafer 10 is held by a lower part 180 of interface 170 (see FIGS. 5 and 8). Each lower part 180 supports the backside of wafer 10 at multiple locations. The lower parts are connected to upper part 171 of the interface 170 (see FIGS. 5, 6 and 7). Interface 170 may be radially symmetric and may be coupled to and rotated by a rotating mechanism such as rotating engine 150 of FIGS. 5 and 7. The interface 170 may be a non-radially symmetrical frame.

The interface 170 may include different interface portions for supporting substrates of different sizes. Each interface portion includes a upper part positioned above the wafer and a lower part that contacts the backside of the wafer.

Figure 9:
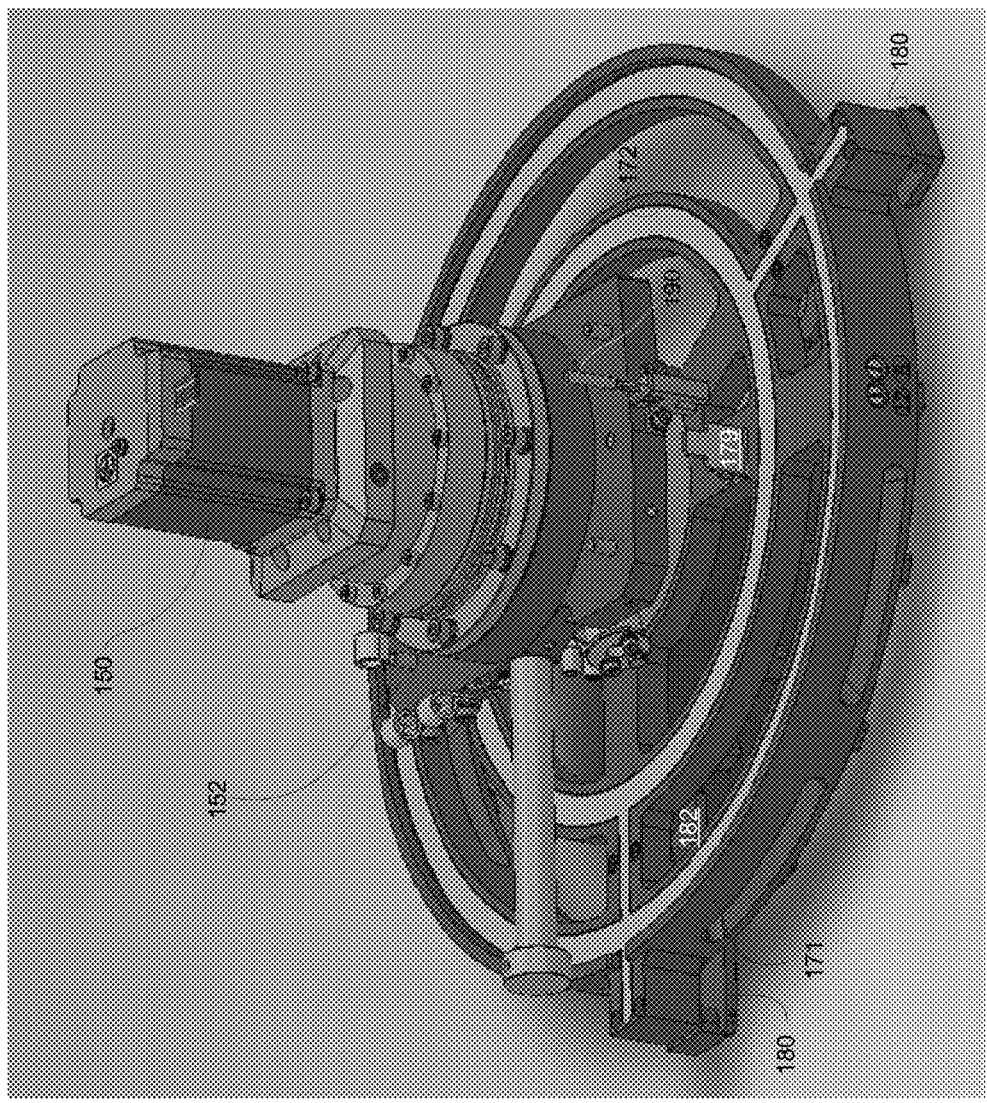
FIG. 9 illustrates a portion of an inspection system according to an embodiment of the invention.
Figure 10:
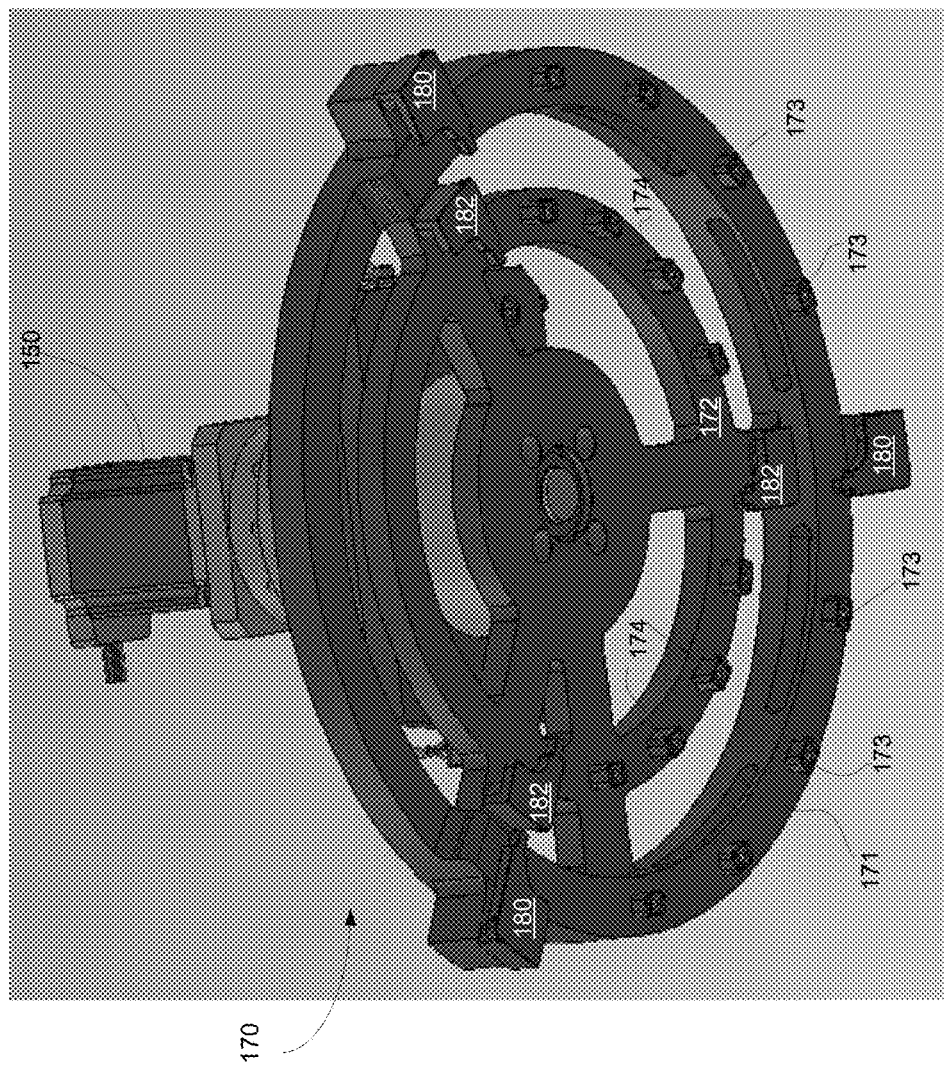
FIG. 10 illustrates a portion of an inspection system according to an embodiment of the invention.
Figure 11:
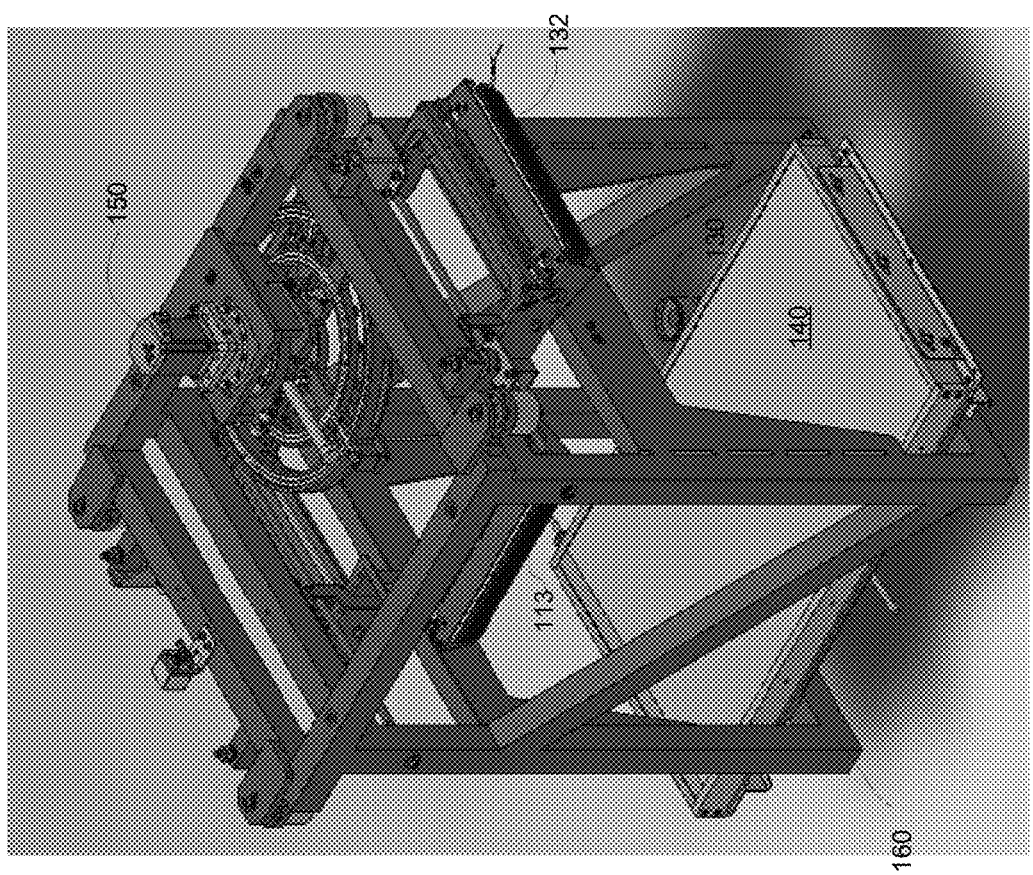
FIG. 11 illustrates a portion of an inspection system according to an embodiment of the invention.
Figure 12:
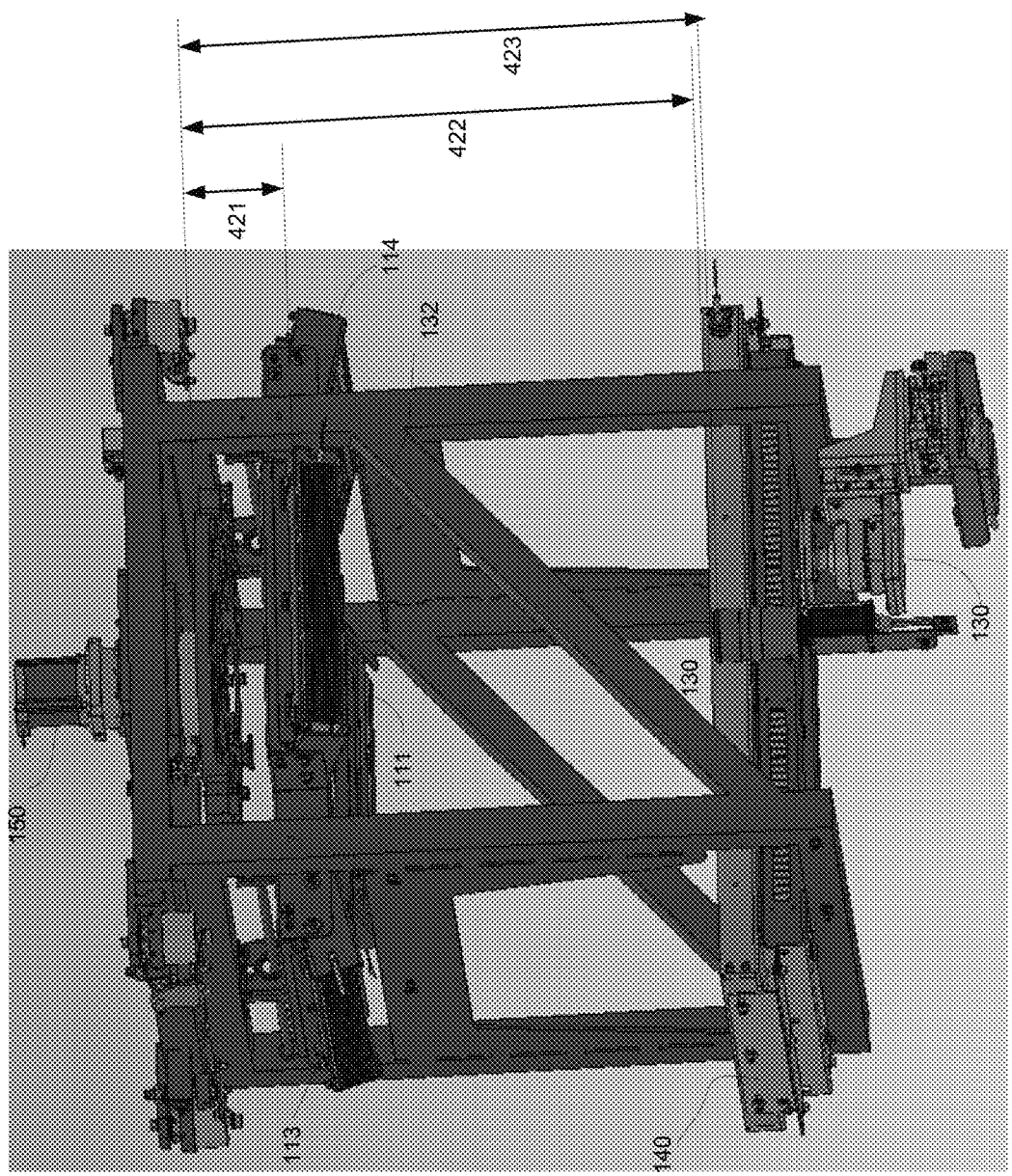
FIG. 12 illustrates a portion of an inspection system according to an embodiment of the invention.

FIGS. 5, 9 and 10 illustrates a first upper part 171 that is connected to three lower parts 180 and a second upper part 172 that is connected to three lower parts 182.

First upper part 171 is bigger than second upper part 172 and may be lower than the second upper part 172—although other spatial relationships may exist between the first and second upper parts 171 and 172. The first and second upper parts 171 and 172 may be coaxial. In FIGS. 5, 9 and 10 the lower parts 180 and 182 has an "L" cross section. Other cross sections may be provided.

A mechanical structure such as rectangular shaped frame such as frame 160 supports the dark field light sources 111, 112, 113 and 114, camera 130, flat dome and rotating engine.

The mechanical structural may have other shapes. The dark field light sources may include a linear array of light emitting diodes (LEDs), the bright field source may include a two dimensional array of LEDs, any number of dark field and/or bright field light sources may be used.

It should be noted that the inspection of wafer backside is positioned as bottom side, thus not requiring wafer flipping The camera optical axis may be perpendicular to the wafer, thus maintaining high image quality without distortion nor defocus over the field of view The camera optical axis may be aligned in a way to cross the wafer plane outside of the effective inspected wafer area in each image, thus avoiding self-reflection of the camera in the effective inspected wafer area.

The wafer holding frame may be equipped with alignment targets such as upper alignment target 179 (see FIG. 9) and lower alignment targets (see lower alignment targets 173 and 174 of FIG. 10).

The upper alignment target 179 faces upwards and is sensed by an alignment sensor 190 during an alignment process in which the wafer is rotated to be aligned to the initial position of the wafer (when the wafer was provided to the interface 170).

The lower alignment targets 173 and 174 are seen in the captured images and are used when merging images of the different parts of the wafer and with different imaging\illumination conditions to form a multi band\multi spectral representation of the wafer surface.

A certain condition of lighting and imaging may be used to capture the alignment target features (position and orientation) in order to provide a basis for creation of a co-ordinate system fixed in relation to the wafer but independent of the actual wafer features. Thus, allowing the use of imaging and illumination techniques beneficial for defect inspection but not exposing fixed features of the wafer that are needed for registration and merging of the multiple positioned images together.

The mentioned above systems and methods may capture images of different spectral bands using either narrow bands illumination (e.g. R, G, B) or "white" illumination in conjunction to spectral band filters in front of the imaging lens.

Figure 13:
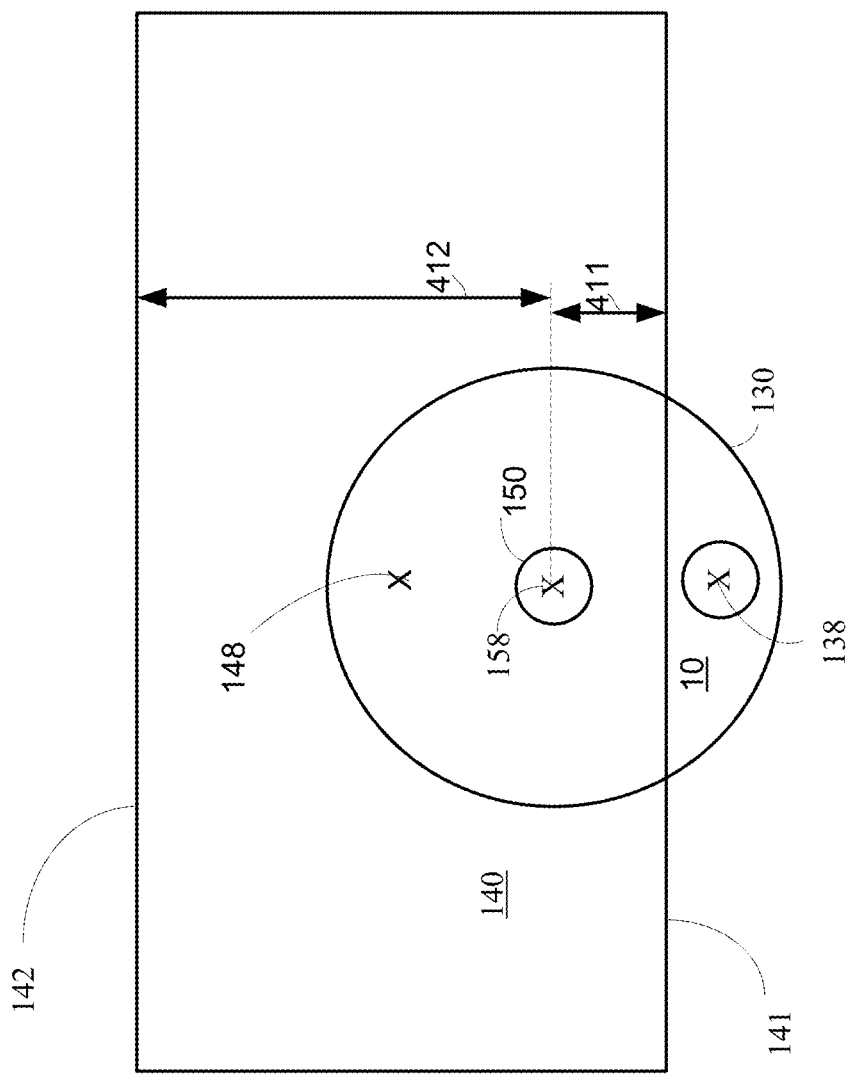
FIG. 13 illustrates various portions of an inspection system according to an embodiment of the invention.

FIG. 13 illustrates various spatial relationships between the camera, the bright field light source 140 and the rotating engine 150 according to an embodiment of the invention.

The rotational axis of the rotating engine 150 is denoted 158. The center of the bright field light source 140 is denoted 148. The optical axis of the camera 130 is denoted 138.

Camera 130 is closer to a first side 141 of bright field light source 140 than to a second side 142 of bright field light source 140.

The optical axis of the camera 138 is positioned outside the vertical projection of the wafer 10.

FIG. 13 illustrates that the optical axis of the camera 130, the center 148 of the bright field light source, the center of the wafer and the rotational axis 158 of the rotating engine 150 may be aligned together along the Y axis of FIG. 13 and may be positioned symmetrically with the X axis of FIG. 13.

Figure 14:
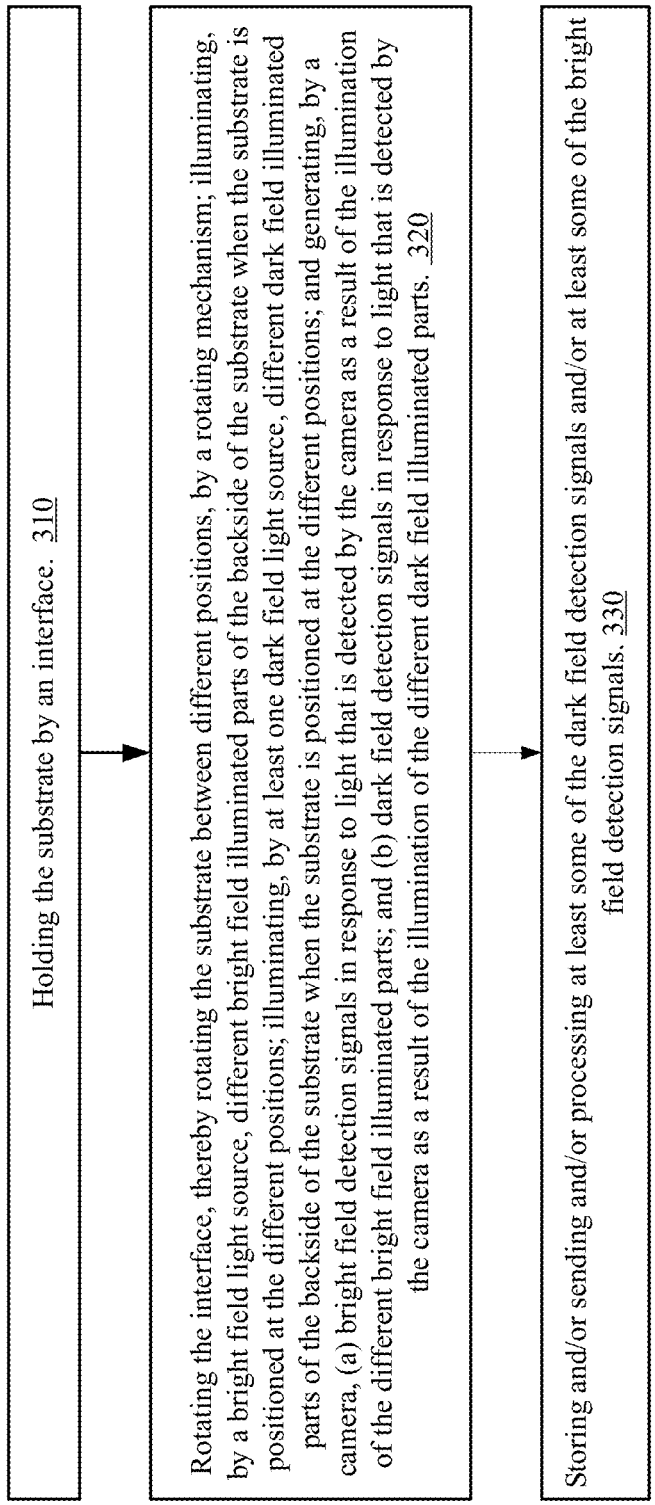
FIG. 14 illustrates a method according to an embodiment of the invention.

FIG. 14 illustrates method 300 according to an embodiment of the invention.

Method 300 includes step 310 of holding the substrate by an interface.

Step 310 is followed by step 320 of rotating the interface, thereby rotating the substrate between different positions, by a rotating mechanism; illuminating, by a bright field light source, different bright field illuminated parts of the backside of the substrate when the substrate is positioned at the different positions; illuminating, by at least one dark field light source, different dark field illuminated parts of the backside of the substrate when the substrate is positioned at the different positions; and generating, by a camera, (a) bright field detection signals in response to light that is detected by the camera as a result of the illumination of the different bright field illuminated parts; and (b) dark field detection signals in response to light that is detected by the camera as a result of the illumination of the different dark field illuminated parts.

Step 320 may be followed by step 330 of storing and/or sending and/or processing at least some of the dark field detection signals and/or at least some of the bright field detection signals.

Step 330 may include reconstructing bright field images and/or reconstructing dark field images and/or processing the bright field images and/or processing the dark field images. The processing may include applying one or more defect detection algorithms, one or more inspection recipes, and the like. The processing may be done in order to detect defects and/or evaluate the quality of the backside of the wafer. the detection algorithms may use the multi positioned merged images from each illumination\imaging condition ("bands") to detect defects in each "band" separately or by combining information between the different bands in order to better detect and\or reject nuisance\false call defects.

Figure 15:
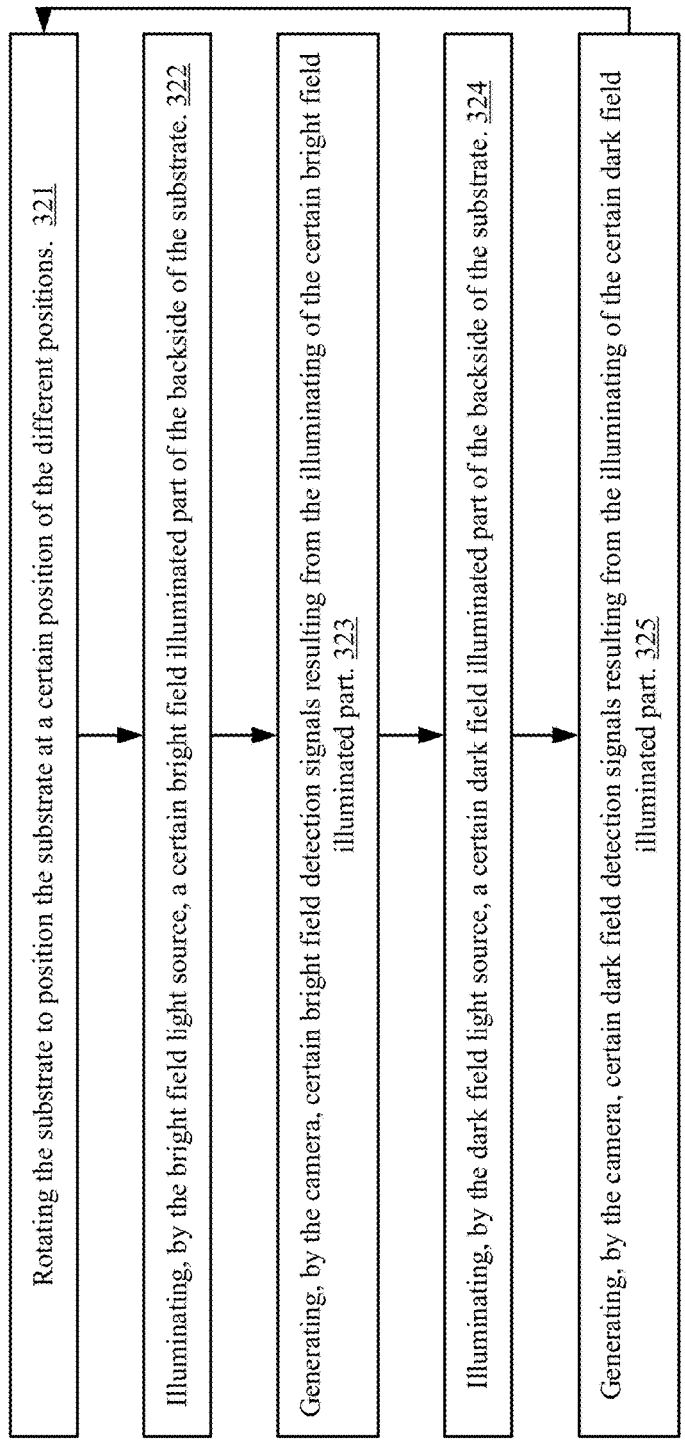
FIG. 15 illustrates a step of the method of FIG. 14 according to an embodiment of the invention.

FIG. 15 illustrates step 320 according to an embodiment of the invention

Step 320 include multiple repetitions of the following steps:

Step 321 of rotating the substrate to position the substrate at a certain position of the different positions. The rotating may be replaced by another type of movement.

Step 322 of illuminating, by the bright field light source, a certain bright field illuminated part of the backside of the substrate.

Step 323 of generating, by the camera, certain bright field detection signals resulting from the illuminating of the certain bright field illuminated part.

Step 324 of illuminating, by the darkfield light source, a certain dark field illuminated part of the backside of the substrate.

Step 325 of generating, by the camera, certain dark field detection signals resulting from the illuminating of the certain dark field illuminated part. Illumination may be done by operating any possible combination out of the four dark field light sources at a time.

Step 325 may be followed by another iteration of steps 321-325 in which a new part of the backside of the substrate is illuminated and by steps where different illumination combination are operated FIG. 15 illustrates a sequence of steps. It is noted that the steps may be executed at other orders. For example, steps 322 and 323 may follow steps 324 and 325. Yet for another example, steps 322 and 324 may be executed in parallel or in at least a partially overlapping manner.

The mentioned above systems and methods may implement adjustable focus and/or zoom lens.

The mentioned above systems and methods may capture images in strobe illumination while wafer is continuously rotating.

Although the following text refers to a backside of the wafer the suggested methods and systems are applicable to the inspection of front side of the wafer and/or of inspection of both front side and backside of the wafer.

The inspection of the front side of the wafer can be obtained by flipping the wafer or otherwise directing the front side of the wafer towards the bright field and dark field light sources.

Inspecting both the backside and the front side of the wafer without flipping the wafer may require an additional camera, bright field and dark field sources that are positioned above the wafer and also will require an interface and a rotating mechanism that will not conceal the wafer. The wafer may be held by an interface with a low footprint (for example a frame that surrounds the wafer and only contacts the wafer at different points) and the rotation mechanism may be position at the side of the wafer.

Furthermore, those skilled in the art will recognize that boundaries between the functionality of the above described operations are merely illustrative. The functionality of multiple operations may be combined into a single operation, and/or the functionality of a single operation may be distributed in additional operations. Moreover, alternative embodiments may include multiple instances of a particular operation, and the order of operations may be altered in various other embodiments.

Multiple different bright filed and or dark field illumination intensities and spectral ranges might be used, together with control of the camera parameters to generated additional dimensions of information of the wafer surface to provide for different detection tasks for different geometric regions of the wafer (central region, near edge region) and\or to provide synthetically increased dynamic range per pixel.

Thus, it is to be understood that the architectures depicted herein are merely exemplary, and that in fact many other architectures can be implemented which achieve the same functionality. In an abstract, but still definite sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

However, other modifications, variations, and alternatives are also possible. The specifications and drawings are, accordingly, to be regarded in an illustrative rather than in a restrictive sense.

The word "comprising" does not exclude the presence of other elements or steps then those listed in a claim. It is understood that the terms so used are interchangeable under appropriate circumstances such that the embodiments of the invention described herein are, for example, capable of operation in other orientations than those illustrated or otherwise described herein.

Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe.

Thus, these terms are not necessarily intended to indicate temporal or other prioritization of such elements. The mere fact that certain measures are recited in mutually different claims does not indicate that a combination of these measures cannot be used to advantage.

We claim:

1. An inspection system for inspection a surface of a substrate, the inspection system comprises:
   an interface for holding the substrate;
   a moving mechanism for moving the interface, thereby moving the substrate between different positions;
   a bright field light source that is configured to illuminate different bright field illuminated parts of the surface of the substrate when the substrate is positioned at the different positions;
   at least one dark field light source that is configured to illuminate different dark field illuminated parts of the surface of the substrate when the substrate is positioned at the different positions; and
   a camera that is configured to: (a) generate bright field detection signals in response to light that is detected by the camera as a result of the illumination of the different bright field illuminated parts; and (b) generate dark field detection signals in response to light that is detected by the camera as a result of the illumination of the different dark field illuminated parts;
   wherein light that is detected by the camera as the result of the illumination of the different bright field illuminated parts and as the result of the illumination of the different dark field illuminated parts does not include an image of the camera;
   wherein the surface of the substrate is a backside of the substrate; and
   wherein at least one of the following is true:
      a. the multiple dark field light sources are a first dark field source, a second dark field source, a third dark field source, and a fourth dark field source; wherein the first dark field source is parallel to the third dark field source; wherein the second dark field source is parallel to the fourth dark field source; and wherein the first dark field source is is perpendicular to the second dark field source;
      b. an axis of rotation of the interface virtually crosses the bright field light source at a second crossing point that is spaced apart from a center of the bright field light source;
      c. the camera and the bright field light source are positioned at substantially a same distance from a substrate backside plane in which the backside of the substrate is located; and
      d. a distance between the dark field light source and the substrate backside plane is smaller than a distance between the camera and the substrate backside plane and is smaller than the distance between the bright field light source and the substrate backside plane.

2. The inspection system according to claim 1 wherein the moving mechanism is a rotating mechanism for rotating the interface thereby rotating the substrate between different positions.

3. The inspection system according to claim 1, wherein the at least one dark field light source and the bright field light source are configured to illuminate the backside of the substrate in a non-overlapping manner.

4. The inspection system according to claim 1, wherein the substrate is positioned at the different positions during different time periods; and wherein during at least one time period the bright field light source and the at least one dark field light source are configured to concurrently illuminate the backside of the substrate.

5. The inspection system according to claim 1, wherein for each bright field illuminated part of the different bright field illuminated parts, when the bright field illuminated part is illuminated, an optical axis of the camera virtually crosses a substrate backside plane the at a first crossing point that is located outside the bright field illuminated part; and wherein the backside of the substrate is located within the substrate backside plane.

6. The inspection system according to claim 1, wherein for each dark field illuminated part of the different dark field illuminated parts, when the dark field illuminated part is illuminated, an optical axis of the camera virtually crosses a substrate backside plane the at a crossing point that is located outside the dark field illuminated part; and wherein the backside of the substrate is located within the substrate backside plane.

7. The inspection system according to claim 1, wherein the interface comprises different interface portions for supporting substrates of different sizes.

8. The inspection system according to claim 1, wherein the different interface portions are coaxial and are positioned at different heights.

9. The inspection system according to claim 1, comprising an alignment sensor and a controller; wherein the interface comprises an alignment target; wherein alignment sensor is configured to detect the alignment target; and wherein the controller is configured to control the movement mechanism in response to detection signals from the alignment sensors.

10. The inspection system according to claim 9, wherein the controller is configured to maintain an alignment between an orientation of the substrate when the substrate is received by the inspection system and between an orientation of the substrate at an end of an inspection of the substrate.

11. The inspection system according to claim 1, wherein the bright field light source is a flat dome that faces the backside of the substrate.

12. The inspection system according to claim 1, wherein the at least one dark field light source comprises multiple dark field light sources.

13. The inspection system according to claim 12, wherein multiple dark field light sources are configured to illuminate the backside of the substrate from different directions.

14. The inspection system according to claim 1, wherein the multiple dark field light sources are the first dark field source, the second dark field source, the third dark field source, and the fourth dark field source; wherein the first dark field source is parallel to the third dark field source; wherein the second dark field source is parallel to the fourth dark field source; and wherein the first dark field source is is perpendicular to the second dark field source.

15. The inspection system according to claim 12, wherein the multiple dark field light sources, the bright field light source and the camera are mechanically coupled to a supporting structure.

16. The inspection system according to claim 15, wherein the supporting structure is a frame; wherein most of the bright field light source is positioned within the frame; and wherein the camera and at least one of the multiple dark field light sources are positioned outside the frame.

17. The inspection system according to claim 15, wherein the substrate, when held by the interface, is positioned directly above a portion of the bright field light source.

18. The inspection system according to claim 12, wherein multiple dark field light sources are arranged in an asymmetrical manner in relation to an axis of rotation of the interface.

19. The inspection system according to claim 1, wherein the axis of rotation of the interface virtually crosses the bright field light source at the second crossing point that is spaced apart from the center of the bright field light source.

20. The inspection system according to claim 19, wherein the bright field light source has a first side and a second side that are opposite to each other; wherein the camera is closer to the first side of the bright field light source; and wherein a distance between the second crossing point and the camera is a fraction of a distance between the second crossing point and the second side of the bright field light source.

21. The inspection system according to claim 1, wherein the camera and the bright field light source are positioned at substantially the same distance from the substrate backside plane.

22. The inspection system according to claim 1, wherein the distance between the dark field light source and a substrate backside plane is smaller than the distance between the camera and the substrate backside plane and is smaller than the distance between the bright field light source and the substrate backside plane.

23. The inspection system according to claim 1, wherein the movement mechanism is configured to rotate the substrate by a rotation that substantially equals half a cycle between one position of the different positions to another position of the different positions.

24. The inspection system according to claim 1, wherein the movement mechanism is configured to rotate the substrate by a rotation that substantially equals a fraction of a cycle between one position of the different positions to another position of the different positions, wherein the fraction of the cycle is smaller than half a cycle.

25. The inspection system according to claim 1, wherein an optical axis of the camera is normal to the backside of the substrate.

26. The inspection system according to claim 1, wherein a shape of the backside of the substrate substantially equals a circle; wherein at least some of the dark field illuminated parts and the bright field illuminated parts have a shape that delimited by a single chord and an arc that is connected to the single chord; and wherein the single chord is smaller than a diameter of the backside of the substrate.

27. The inspection system according to claim 1, comprising a processor that is configured to process the bright field detection signals and the dark field detection signals.

28. The inspection system according to claim 1, comprising 1 processor that is configured to reconstruct one or more images of the substrate; wherein the one or more images comprises a bright field image of the backside of the substrate and a dark field image of the backside of the substrate.

29. The inspection system according to claim 1, comprising a processor; wherein the processor is configured to reconstruct a bright field image of the backside of the substrate from bright field detection signals related to the different bright field illuminated parts of the backside of the substrate.

30. The inspection system according to claim 29, wherein the interface comprises alignment targets; wherein the processor is configured to reconstruct the bright field image of the backside of the substrate based on bright field detection signals related to the alignment targets.

31. The inspection system according to claim 30, comprising a processor; wherein the processor is configured to reconstruct bright field images of the different bright field illuminated parts of the backside of the substrate from the bright field detection signal related to the different bright field illuminated parts of the backside of the substrate; wherein the bright field images of the different bright field illuminated parts of the backside of the substrate comprise images the alignment target.

32. The inspection system according to claim 31, wherein the processor is configured to merge the bright field images of the different bright field illuminated parts of the backside of the substrate to provide the bright field image of the backside of the backside; wherein the merging is responsive to the images of the alignment targets.

33. An inspection system for inspection a surface of a substrate, the inspection system comprises:
  an interface for holding the substrate; wherein the interface comprises alignment targets;
  wherein the interface comprises different interface portions for supporting substrates of different sizes; wherein each of the different interface portions comprises a subset of the alignment targets;
  a moving mechanism for moving the interface, thereby moving the substrate between different positions;
  a bright field light source that is configured to illuminate different bright field illuminated parts of the surface of the substrate when the substrate is positioned at the different positions;
  at least one dark field light source that is configured to illuminate different dark field illuminated parts of the surface of the substrate when the substrate is positioned at the different positions;
  a processor; and
  a camera that is configured to: (a) generate bright field detection signals in response to light that is detected by the camera as a result of the illumination of the different bright field illuminated parts; and (b) generate dark field detection signals in response to light that is detected by the camera as a result of the illumination of the different dark field illuminated parts;
  wherein light that is detected by the camera as the result of the illumination of the different bright field illuminated parts and as the result of the illumination of the different dark field illuminated parts does not include an image of the camera;
  wherein the surface of the substrate is a backside of the substrate;
  wherein the processor is configured to reconstruct a bright field image of the backside of the substrate from bright field detection signals related to the different bright field illuminated parts of the backside of the substrate;
  wherein the processor is configured to reconstruct the bright field image of the backside of the backside of the substrate based on bright field detection signals related to the alignment targets.

34. A method for inspecting a surface of a substrate, the method comprises:
  holding the substrate by an interface;
  moving the interface, thereby moving the substrate between different positions, by a movement mechanism;
  illuminating, by a bright field light source, different bright field illuminated parts of the surface of the substrate when the substrate is positioned at the different positions;
  illuminating, by at least one dark field light source, different dark field illuminated parts of the surface of the substrate when the substrate is positioned at the different positions; and
  generating, by a camera, (a) bright field detection signals in response to light that is detected by the camera as a result of the illumination of the different bright field illuminated parts; and (b) dark field detection signals in response to light that is detected by the camera as a result of the illumination of the different dark field illuminated parts; and
  wherein light that is detected by the camera as the result of the illumination of illumination of the different bright field illuminated parts and as the result of the illumination of the different dark field illuminated parts does not include an image of the camera;
  wherein the surface of the substrate is a backside of the substrate; and
  wherein at least one of the following is true:
    a. the multiple dark field light sources are a first dark field source, a second dark field source, a third dark field source, and a fourth dark field source; wherein the first dark field source is parallel to the third dark field source; wherein the second dark field source is parallel to the fourth dark field source; and wherein the first dark field source is is perpendicular to the second dark field source;
    b. an axis of rotation of the interface virtually crosses the bright field light source at a second crossing point that is spaced apart from a center of the bright field light source;
    c. the camera and the bright field light source are positioned at substantially a same distance from a substrate backside plane in which the backside of the substrate is located; and
    d. a distance between the dark field light source and the substrate backside plane is smaller than a distance between the camera and the substrate backside plane and is smaller than the distance between the bright field light source and the substrate backside plane.

35. The method according to claim 34, wherein the surface of the substrate is a backside of the substrate.

* * * * *